US009851360B2

(12) United States Patent
Inciardi et al.

(10) Patent No.: US 9,851,360 B2
(45) Date of Patent: Dec. 26, 2017

(54) SELF CONTAINED IN-VITRO DIAGNOSTIC DEVICE

(71) Applicant: iMPak Health, LLC, Neptune, NJ (US)

(72) Inventors: Salvatore Richard Inciardi, Manalapan, NJ (US); Sandra D. Elliott, Barnegat, NJ (US); Jonas Sven-Erik Tiren, Uppsala (SE); Per Nathanaelson, Taby (SE); Jakob Ehrensvard, Stockholm (SE)

(73) Assignee: iMPak Health, LLC, Neptune, NJ (US)

( * ) Notice: Subject to any disclaimer, the term of this patent is extended or adjusted under 35 U.S.C. 154(b) by 744 days.

(21) Appl. No.: 14/212,219

(22) Filed: Mar. 14, 2014

(65) Prior Publication Data

US 2014/0220666 A1 Aug. 7, 2014

Related U.S. Application Data

(62) Division of application No. 13/069,348, filed on Mar. 22, 2011, now Pat. No. 8,673,214.

(51) Int. Cl.
  *G01N 21/01* (2006.01)
  *G01N 33/66* (2006.01)
  *A61B 5/145* (2006.01)
  *A61B 5/00* (2006.01)

(52) U.S. Cl.
  CPC ......... *G01N 33/66* (2013.01); *A61B 5/14532* (2013.01); *A61B 5/0002* (2013.01); *A61B 2560/0406* (2013.01); *A61B 2562/18* (2013.01); *Y10T 436/104998* (2015.01); *Y10T 436/144444* (2015.01)

(58) Field of Classification Search
  CPC .......... G01N 21/01; G01N 2021/0112; G01N 2021/0118; G01N 27/416
  See application file for complete search history.

(56) References Cited

U.S. PATENT DOCUMENTS

| 5,580,794 | A | | 12/1996 | Allen | |
|---|---|---|---|---|---|
| 6,153,085 | A | * | 11/2000 | Patko | ............... G01N 33/48785 204/400 |
| 7,768,645 | B2 | * | 8/2010 | Roman | ............. G01N 21/8483 356/406 |
| 2003/0023189 | A1 | | 1/2003 | Kuo | |

(Continued)

OTHER PUBLICATIONS

International Search Report for International Application No. PCT/US2011/029480 which is the corresponding application to the Instant application.

*Primary Examiner* — Jan Ludlow
(74) *Attorney, Agent, or Firm* — Law Offices of Robert F. Zielinski, LLC

(57) ABSTRACT

A portable apparatus for measuring a glucose level of a user having: a card-like member; a processor within the card-like member; at least one glucose sensor comprising a reagent, the glucose sensor generating a signal indicative of a measured glucose level upon application of a blood sample to the glucose sensor, wherein the glucose sensor is fixed to the card-like member and operably coupled to the processor; and at least one cover alterable between a first position in which the glucose sensor is covered and a second position in which the glucose sensor is exposed for use.

27 Claims, 7 Drawing Sheets

(56) References Cited

U.S. PATENT DOCUMENTS

| | | |
|---|---|---|
| 2005/0143675 A1 | 6/2005 | Neel |
| 2006/0258929 A1* | 11/2006 | Goode, Jr. .......... A61B 5/0031 |
| | | 600/345 |
| 2007/0015983 A1 | 1/2007 | Werner |
| 2007/0243634 A1* | 10/2007 | Pamula .............. B01F 13/0071 |
| | | 436/518 |
| 2008/0234562 A1 | 9/2008 | Jina |
| 2009/0018426 A1 | 1/2009 | Markle |
| 2010/0009456 A1 | 1/2010 | Prins |

* cited by examiner

SELF CONTAINED IN-VITRO DIAGNOSTIC DEVICE

CROSS-REFERENCE TO RELATED APPLICATIONS

This application is a Divisional application of U.S. patent application Ser. No. 13/069,348 filed Mar. 22, 2011, issued as U.S. Pat. No. 8,673,214 on Mar. 18, 2014 which claims the benefit of U.S. Provisional Application No. 61/316,002, filed on Mar. 22, 2010, the entireties of which is hereby incorporated by reference.

FIELD OF THE INVENTION

The present invention relates to a self-contained in-vitro diagnostic device, and specifically to a disposable diagnostic device that has fixed sensors.

BACKGROUND OF THE INVENTION

Diabetes is a disease in which the body does not produce or properly use insulin. Insulin is a hormone that is needed to convert sugar, starches and other food into glucose, which is the fuel cells need for on-going activity. Published studies indicate that at least 7% of the US population has diabetes, and about 70% of those with diabetes have been diagnosed. About 5-10% of all diabetics have Type I diabetes in which the pancreatic cells that produce insulin have been destroyed. Thus, there are no cells to produce the chemical that produces insulin. Type I diabetes is treated by supplying insulin by injection or pump. The balance of those with diabetes have Type II diabetes in which pancreatic cells produce insulin, but other cells in the body do not use insulin well to convert food into glucose. Type II diabetes is treated by diet, exercise, oral medications, insulin, or a combination thereof.

While diabetes cannot yet be cured, it can be controlled. If it is not controlled, complications result. For example, adults with diabetes have heart disease rates about 2 to 4 times higher than adults without diabetes. The risk for stroke is 2 to 4 times higher among people with diabetes. Diabetes is the leading cause of new cases of blindness among adults aged 20-74 and the leading cause of kidney failure. About 60-70% of people with diabetes have mild to severe forms of nervous system damage. The result of such damage includes impaired sensation or pain in the feet or hands, which may eventually result in amputation of the limb. In addition, people with diabetes are more susceptible to many other illnesses and, once they acquire these illnesses, often have worse prognoses than non-diabetics.

As it stands, if an adult or child would like to know if they are at risk for diabetes, they are required to contact their physician, schedule an appointment, subject themselves to blood tests and then report back to their physician when the results are obtained. This process can be both an expensive and time consuming process for the patient. Due to the cost of both time and money, many individuals forgo proper testing and are therefore not properly diagnosed. Further, this process is made even more difficult for those without primary care physicians or medical insurance to pay for the appointments and testing that is required. Therefore, the remains a need for a self-contained in-vitro diagnostic device that is inexpensive, can be used easily at the home of the patient and provides for a one-time diagnostic check-up.

To control diabetes, it is necessary to monitor the level of glucose in the blood. The frequency of measurement varies from patient to patient, depending on a number of factors including the severity of the disease, type of diabetes, level of physical activity, eating habits, and other health issues. For patients with diabetes, it is often necessary to determine the glucose level in blood several times a day. Consistently taking readings help patients manage their glucose levels better, thereby improving insulin and other therapies and helping to prevent complications.

A common method of blood glucose self-monitoring is to prick a finger or other area to release capillary blood, absorb a minute amount of blood onto a test strip, and insert the test strip into a monitor to measure the amount of glucose in the blood. In particular many devices allow for self assessment of blood glucose for diabetes patients. Many of these devices are small portable diagnostic monitors that use replaceable single-use test strips. By placing a very small volume of blood on such a single use test strip, an electrochemical reaction converts the blood glucose into a small electric current that relatively easily can be converted into a blood glucose value/level within second. These devices further require that the user enter calibration data specific to the test strips being used. Since the prior art devices all require that test strips be entered for each single use, a user is required to enter calibration data each time a new set of test strips is to be used with the device.

Although the current devices typically meet the requirements for disease management of chronic patients, another set of requirements apply in a screening setting, whether for diabetes, high cholesterol, or other physiological conditions. The cost of the device hardware, distribution, training, calibration and data feedback requirements all make the current devices non-practical. Screening therefore typically requires a patient to go to a hospital where a blood sample is taken and the blood sample sent to a laboratory for analysis and testing. Further, it is often desired to have a fasting blood glucose level/value as well as a value after intake of a certain amount of simple sugars, which add timing constraints to the already complicated process. Therefore, there is a need for a device that is economical and self-contained and which allows for a quick screen test in a patient's home environment where the results can be effectively and securely transmitted to a centralized location for diagnosis.

SUMMARY OF THE INVENTION

One aspect of the present invention is a portable apparatus for measuring a glucose level of a user comprising: a card-like member; a processor within the card-like member; at least one glucose sensor comprising a reagent, the glucose sensor generating a signal indicative of a measured glucose level upon application of a blood sample to the glucose sensor, wherein the glucose sensor is fixed to the card-like member and operably coupled to the processor; and at least one cover alterable between a first position in which the glucose sensor is covered and a second position in which the glucose sensor is exposed for use.

Another aspect of the present invention is a portable apparatus for measuring a glucose level of a user comprising: a card-like member; a processor within the card-like member; at least one glucose sensor comprising a reagent, the glucose sensor generating a signal indicative of a measured glucose level upon application of a blood sample to the glucose sensor, wherein the glucose sensor is fixed to the card-like member and operably coupled to the processor; and a memory device within the card-like member and operably coupled to the processor the memory device comprising pre-stored calibration data unique to the glucose sensor.

In yet another aspect of the present invention is a portable apparatus for measuring a physiological condition comprising: a card-like member; a processor within the card-like member; at least one sensor comprising a reagent, the sensor generating a signal indicative of a measured physiological parameter upon application of a blood sample to the sensor, wherein the sensor is fixed to the card-like member and operably coupled to the processor; and at least one cover alterable between a first position in which the sensor is covered and a second position in which the sensor is exposed for use.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
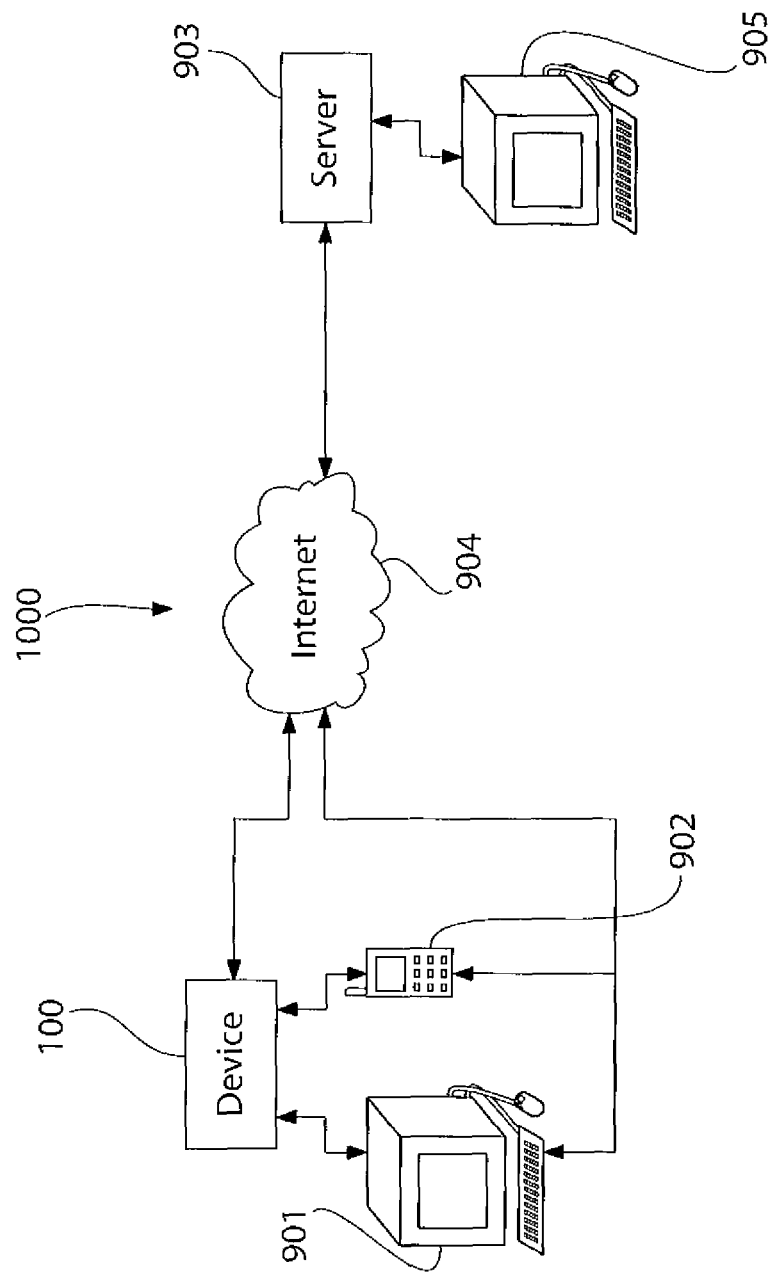
FIG. 1 is a schematic of a system according to one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

In the description of embodiments of the invention disclosed herein, any reference to direction or orientation is merely intended for convenience of description and is not intended in any way to limit the scope of the present invention. Moreover, the features and benefits of the invention are illustrated by reference to exemplified embodiments. Accordingly, the invention expressly should not be limited to such exemplified embodiments illustrating some possible but non-limiting combination of features that may be provided alone or in other combinations of features; the scope of the invention being defined by the claims appended hereto.

Referring to FIG. 1, a schematic of a system 1000 according to an embodiment of the present invention is illustrated. A device 100 obtains a sample from a user, generates a signal relating to a calculated physiological parameter, calculates an actual physiological value relating to the received sample and transmits the actual physiological value and corresponding information to an external device. The external device can be a personal computer 901, a mobile communication device 902 or a remote server 903. The transmission of the actual physiological value can be by means of a wireless communication device located within the device or a wired connection to the external device. In one embodiment, device 100 may simply store the actual physiological value and corresponding information until the device 100 is sent to a centralized data processing and diagnostics site where the device 100 is scanned and the information retrieved. In an alternate embodiment, the physiological parameter may be wirelessly transmitted to a personal computer 901 or mobile communication device 902 at the location of the user, and then transmitted through the internet 904 to a remote server 903 for view on a personal computer 905, such as a personal computer located at a physician or doctor's office.

Figure 2:
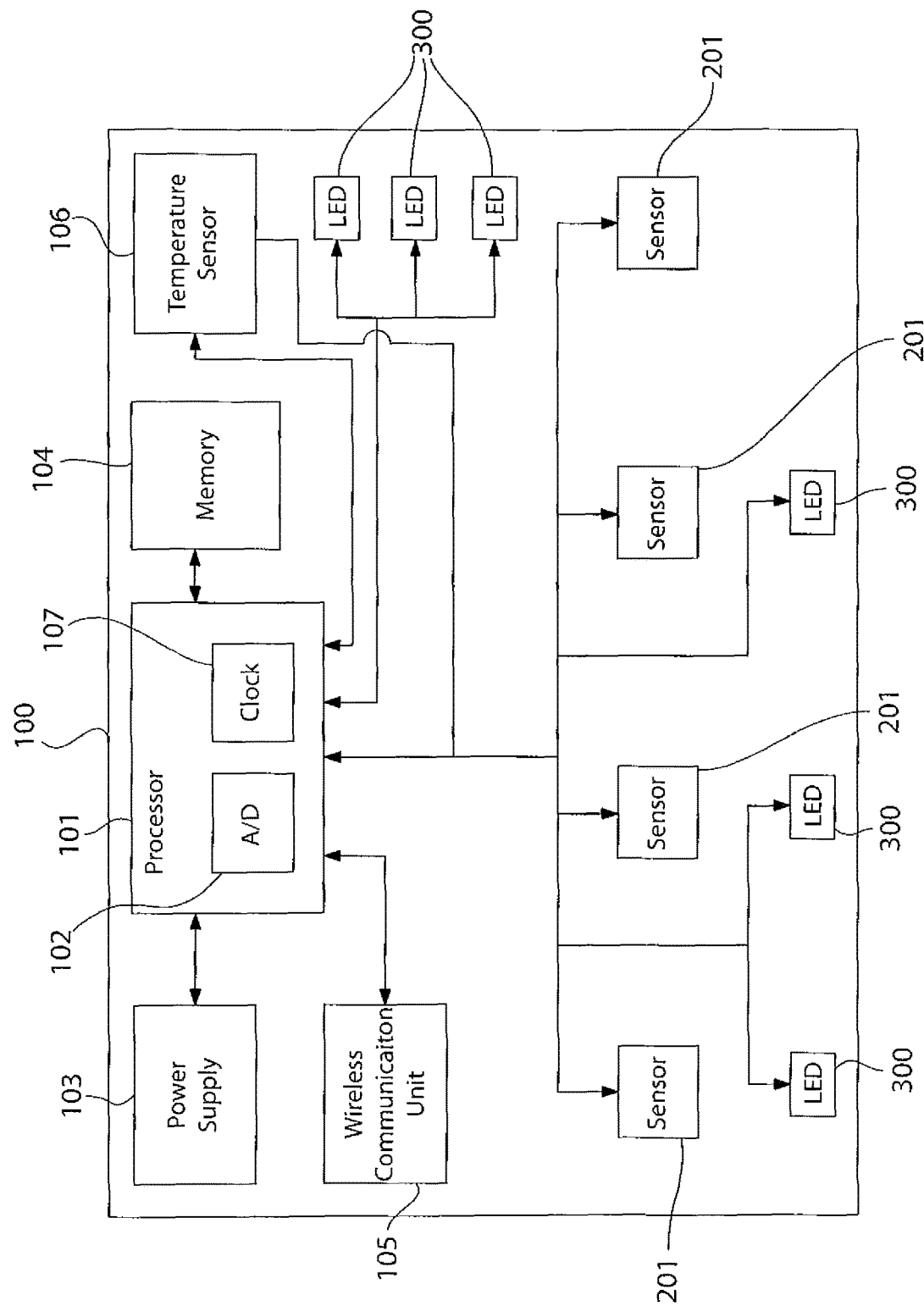
FIG. 2 is a schematic of a device according to one embodiment of the present invention.

Referring to FIG. 2, a schematic of the device 100 according to an embodiment of the present invention is illustrated. The device comprises a processor 101, a power supply 103, a memory unit 104, a wireless communication unit 105, a temperature sensor 106, at least one test site 200 (comprising at least one sensor 201) and at least one indication device 300.

In the exemplified embodiment, the processor 101 comprises signal-conditional means, data processing means, data acquisition means, an analog-to-digital converter (A/D) 102, and an internal clock 107. The processor 101 is operably coupled to and configured to control the interaction of the power supply 103, the memory unit 104, the wireless communication unit 105, the temperature sensor 106, the at least one test site 200, the at least one sensor 201 and the at least one indication device 300. Specifically, the processor 101 must be configured to the specific properties of the at least one sensor 201 configured within the device 100. The clock 107 is configured to provide time-keeping means to allow each measurement of the device 100 to be time-stamped and stored in the memory unit 104. The power supply 103 is operably coupled to and configured to supply power to the processor 101, the memory unit 104, the wireless communication unit 105, the temperature sensor 106, the at least one test site 200, the at least one sensor 201 and the at least one indication device 300. The memory unit 104 is operably coupled to the processor 101 and configured to store data. In one embodiment, the memory unit 104 may be a non-volatile memory unit.

The wireless communication unit 105 is operably coupled to and configured to transmit data wirelessly to an external device. In one embodiment, the wireless communication device 105 comprises an integrated planar antenna. Further, in one embodiment, the wireless communication device 105 uses radio frequency identification (RFID) to communication with the external device. The wireless communication device 105 may use active, passive, or semi-passive RFID technologies. In alternate embodiments, the wireless communication device 105 may be a Bluetooth® enabled device or Zigbee® enabled device. Further, in other alternate embodiments, the wireless communication device 105 may be a device that uses any other non-proprietary wireless protocol for wireless communication. It should be noted that in alternate embodiments, the wireless communication device may be omitted and the device may comprise various ports for wired connections to the external device. Since the information being transmitted by the wireless communication device 105 may be confidential, optional cryptographic operations can be performed prior to data exchange, so that only a legitimate receiver can decrypt and verify the data retrieved from the device 100.

As noted above, the present invention provides for at least one temperature sensor 106 (e.g., a thermistor, thermometer, or thermocouple device) which is used to measure temperature at the site of the sensor 201, along with the ambient temperature. As with any chemical sensing method, transient changes in temperature during or between measurement cycles can alter background signal, reaction constants and/or diffusion coefficients. Accordingly, the temperature sensor 106 is used to monitor changes in temperature over time. A maximum temperature change over time threshold value can be used to invalidate a measurement of a sensor 201. Such a threshold value can, of course, be set at any objective level, which in turn can be empirically determined depending upon the sensor 201 used, how the temperature measurement is obtained, and the physiological parameter being detected. In the illustrated embodiment of FIGS. 3 and 4, the design of the device 100 gives a reasonable isothermal environment and the temperature sensor 105 may provide a signal proportional to the temperature at the sensor 201 site to the processor 101.

Absolute temperature threshold criteria can also be detected by the temperature sensor 106, wherein detection of high and/or low temperature extremes can be used in a data screen to invalidate a measurement by a sensor 201. The temperature sensor 106, for example, may provide a voltage proportional to the temperature to the A/D converter 102 of the processor 101 of the device 100, which can then make a determination as to whether the temperature of the testing environment is within predetermined thresholds, and signal an indication device 300 if accuracy would be negatively affected.

Figure 3:
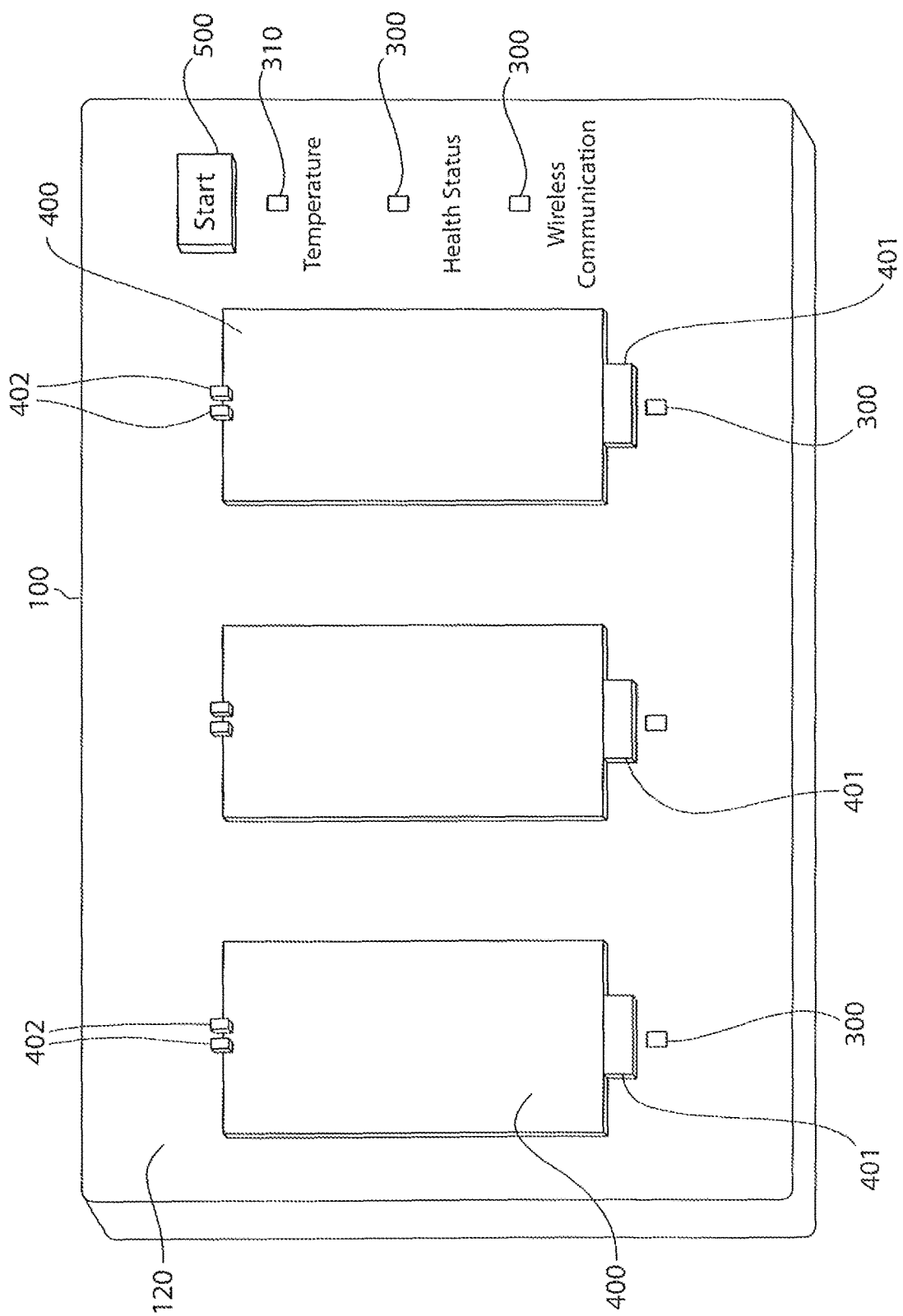
FIG. 3 is a perspective view of the device of FIG. 2 with the covers disposed on top of the sensors according to one embodiment of the present invention.
Figure 4:
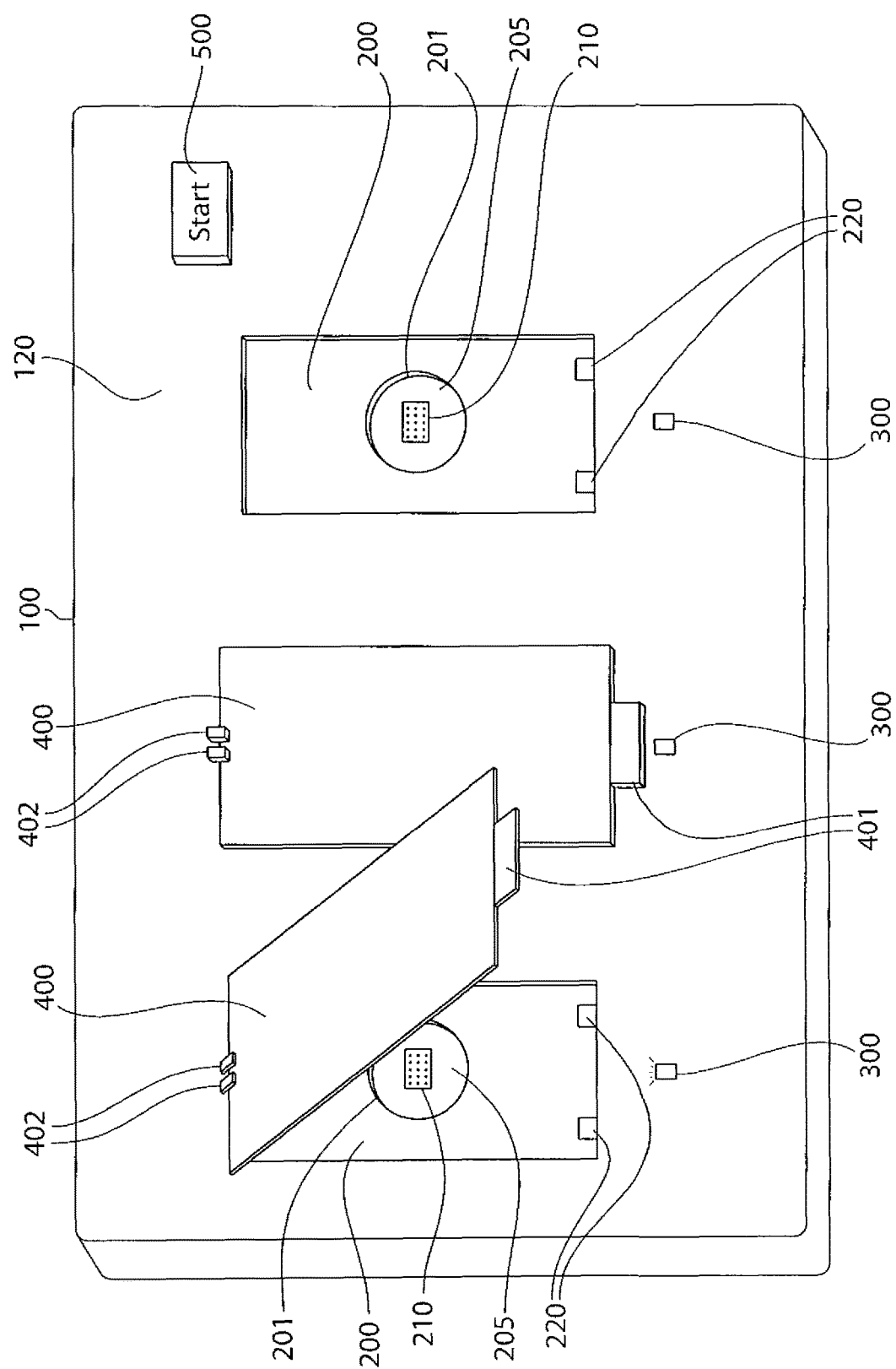
FIG. 4 is a perspective view of the device of FIG. 2 wherein one sensor is illustrated with a cover disposed on top, another sensor is illustrated with a cover in a second position, and yet another sensor with the cover removed completely according to another embodiment of the present invention.

Referring to FIGS. 3 and 4, a device 100 according to one embodiment of the present invention is illustrated. In the exemplified embodiment, the device 100 comprises is a body 120 that is a thin, flat article having opposing planar surfaces that are substantially parallel to each other (referred to herein as a "planar design"). In one embodiment, the body 120 is a card-like member that has a planar design. In alternate embodiments, the surfaces of the device 100 may be contoured or curved, and therefore do not have to be substantially parallel to each other. In one embodiment where the device is of a planar design, one side is perfectly flat and allows for traditional screen-printing techniques to be used to apply the elements/components of the sensors 201. Therefore, the sensors 201 are all configured in the same level and on the same substrate that holds the biosensor chemistry, thereby eliminating all interconnections.

As shown in FIGS. 3 and 4, the device 100 comprises three test sites 200, each test site 200 having a corresponding cover 400. It should be noted that the invention is not limited to the number or type of test sites 200 used in the device 100. Further, in alternate embodiments, the device 100 may have more or less covers 400 than test sites 200.

As illustrated in FIGS. 3 and 4, each test site 200 has a corresponding cover 400 that is secured and disposed on top of the test site 200. The cover 400 comprises a tab 401 and at least one securing piece 402. The cover 400 is configured so that a user may lift on the tab 401 to remove the cover 400 thereby exposing the underlying sensor 201. Further, in the illustrated embodiment, the side of the cover 400 opposing the tab 401 comprises the securing pieces 402. The securing pieces are configured to prevent the cover 400 from being completely removed from the device 100. Therefore, the cover 400 may be configured in and in-between two positions: a first position (shown in FIG. 3) whereby the cover 400 is covering the test site 200 and protecting the sensor 201 from moisture and contamination from the outside environment, and a second position (shown in FIG. 4) wherein the cover 400 is removed from the test site 200 thereby exposing the sensor 201 to the outside environment.

In the exemplified embodiment, the cover 400 is operably configurable between the first and second positions more than one time, so that the cover 400 may first cover the test site 200, then be configured to the second position to expose the sensor 201 for the application of a sample, and then be configured to re-cover the test site 200 so that the sample is contained within the sensor 201. The invention, however, is not so limited and in alternate embodiments the securing pieces 402 may be omitted so that the cover 400 may be completely removable from the device 100. In one embodiment, the cover 400 is a removable seal, and the removable seal is a piece of removable foil. The invention, however, is not so limited and the cover 400 may comprise a hinged structure, a removable seal, or a combination thereof. In embodiments where the cover 400 comprises both a hinged structure and a removable seal, the removable seal is disposed between the sensor and the hinged structure. Further, in alternate embodiments, the tab 401 may be omitted.

In one embodiment, when the cover 400 is disposed on top of a test site 200 (in the first position), the cover 400 may be secured by an adhesive (not shown) that is located either on the cover 400 and/or on a corresponding portion of the body 120 of the device 100. The adhesive preferably creates a moisture tight seal when the cover 400 is in the first position. Further, the adhesive is preferably designed so that the cover 400 may be re-oriented in the first position after being oriented in the second position and still maintain a moisture tight seal over the sensor 201. In an alternate embodiment, the cover 400 may be configured to fully seal the entire test site 200 in an air tight and water tight manner.

In an alternate embodiment, the cover 400 and body 120 may comprise interlocking interfaces that are configured to secure the cover 400 to the body 120 when the cover is in the first position, and allow the cover to be configurable between the first and second positions as described above.

Further, in some embodiments, the device 100 further comprises a small amount of desiccant that is added adjacent to each test site 200 to absorb any moisture that could potential seep into the sensor 201.

As described in more detail below, FIG. 3 illustrates an embodiment of the device 100 of the present invention that comprises three test sites 200, each test site 200 being covered by a corresponding cover 400. FIG. 4 illustrates an embodiment of the device 100 of the present invention that comprises three test sites 200, whereby the first test site 200 has its cover 400 in the second position so that the sensor 201 of the test site 200 is exposed, the second test site 200 is covered by a cover 400 that is in the first position, and the third test site 200 has its cover 400 completely removed so that its test site 200 and sensor 201 are completely exposed. It should be noted that the various states of the covers 400 and test sites 200 of device 100 of FIG. 4 are illustrated to aid in the discussion of the device 100 and its components, and are in no way limited of the invention.

Referring to FIGS. 3-4, the device 100 may comprise one or more test sites 200, each test site 200 comprising a sensor 201 and at least one sensing pad 220. The sensor 201 comprises a cavity 205 and a reagent 210, the reagent 210 being located substantially within the cavity 205. In one embodiment, the sensor 201 is located within a depression on the test site 200. Further, in some embodiments, the sensor 201 is embedded within and affixed to the device 100. Therefore, in some embodiments, the sensors 201 cannot be removed from the device 100. The reagent 210 is configured to alter its properties to enable the sensor 201 to detect and measure a physiological parameter of a sample when the sample is placed within the cavity 205.

It should be noted that the sensor 201 is generically illustrated as a circular shaped area. The invention, however, is not so limited and in alternate embodiments the sensor 201 may be of different sizes and shapes. Further, it should be noted that the cavity 205 is also generically illustrated, and in alternate embodiments the cavity 205 may be of different sizes and shapes. Moreover, it should be noted that the reagent 210 is also generically illustrated as a square, and in alternate embodiments the reagent 210 may be of different sizes and shapes. Further, in alternate embodiments the cavity 205 may be omitted.

As noted above, each sensor 201 is configured to measure a physiological parameter of a sample when the sample is placed in or on the sensor 201. A physiological parameter may be a glucose level/concentration, a cholesterol level/concentration, a blood urea nitrogen (BUN) level/concentration or a creatinine level/concentration. The invention, however, is not so limited and the physiological parameter may be any other value or characteristic relating to an organism's health or function. In one embodiment, the sample is a mammalian blood sample. The invention, however, is not so limited and any sample that comprises a trace of a physiological parameter may be used. For example, in an embodiment where the sensor 201 is designed to measure a glucose level, the reagent 210 may be glucose oxidase, glucose dehydrogenase/pyrroloquinolinequinone, dehydrogenase/nicotinamide-adenine dinucleotide, dehydrogenase/flavin-adenine dinucleotide, or any other compound capable of detecting glucose in a sample.

The sensing pad 220 of the test site 200 is configured to detect when the cover 400 corresponding to the test site 200 is lifted or removed from the first (covered) position and into the second (exposed) position. When the cover 400 of a test site 200 is lifted, the sensing pad 220 sends a signal to the processor 101 of the device 100 and initializes the measurement and sensing processes of the sensor 201 and processor 101. Therefore, when a sample is placed on the sensor 201, the measurement and sensing processes of the sensor 201 and processor 101 are enabled and can detect the presence of the physiological parameter of the sample. As discussed in more detail below, after the sensor 201 senses and measures the physiological parameters of the sample placed thereon, the sensor 201 transmits a signal indicative of the measures physiological parameter to the processor 101 and memory unit 104.

Further, when the cover 400 is lifted, an indication device 300 corresponding to that particular sensor 201 is also initialized. In the exemplified embodiment, the indication device 300 is an LED that is illuminated (either flashing or a steady "on" state) when the cover 400 of the corresponding test site 200 is configured to the second position. The invention, however, is not so limited and in alternate embodiments the indication device 300 may be any other device that can be used to signal information to the user. In one embodiment, after the measurement and sensing processes are completed on the sample, the indication device 300 alters its state (e.g. going from a flashing state to a steady "on" state) to indicated that the sensing and measurement processes are complete. Thereafter, in one embodiment, the user may reconfigure the cover 400 back to the first position so that the sensor 201 and sample are covered and unexposed, and the indication device 300 may turn off after a pre-determined time period to save power. Furthermore, in one embodiment, if the device 100 is turned on again, the indication device 300 corresponding to the used testing site 200 may indicate that the site has already been used (e.g. lighting up in a different color or not lighting up at all).

Depending on the requirements of the particular application of the device 100, a plurality of sensors 201 may be configured on a device 100. The sensors 201 can either be of the same type (meaning they measure the same physiological parameter) or comprise various different reagents 210 to allow a quantitative analysis of more than one physiological parameter using one device 100. In alternate embodiments, the sensors 201 may be biochemical sensors and electrochemical biosensors for detecting a physiological parameter of a sample. In one embodiment, the sensor 201 is a biochemical sensor or an electrochemical biosensor and comprises at least two electrodes and a biochemically active material (reagent) working in a voltammetric setting.

In another embodiment, the sensor 201 and reagent 210 comprise physiological measuring technology that is based upon the well known, mature, reliable, accurate, quick response, non-continuous, test strip based measurement technologies which are sometimes referred to as episodic or intermittent monitoring technologies. Test strip based monitoring systems are considered invasive, i.e. systems which require a capillary blood sample to estimate the individual's blood glucose concentration. Such samples are normally obtained by lancing a finger tip or an approved alternate test site to obtain such a capillary blood sample. Further, these systems are characterized by an electrochemical measurement based upon a reaction with blood glucose that generates an electrical current when read by corresponding electronics of the sensor 201, whose magnitude corresponds to the physiological (e.g. glucose, cholesterol, etc.) concentration of the test sample. In such a system, a user only needs to supply an adequate sample to the reagent 210 within the sensor cavity 205 and wait for the processor 100 to calculate a reading.

As noted above, the processor 101 should be configured to the specific properties of the sensors 201 contained therewith prior to the application of a sample and a measurement of a physiological parameter. Further, since the sensors 201 of the present invention are affixed to or embedded in the device 100, the processor 101 of the device may be pre-calibrated to the specific properties of the specific sensors 201 contained within prior to distribution to a user. It should be noted that during the manufacturing of physiological sensors, small discrepancies result in the properties of the sensors from one lot and sensors of a different lot. In particular, sensors of one manufacturing lot will usually have properties that vary from the properties of sensors of a different manufacturing. The specific properties that can vary include, but are not limited to, the specific concentration of reagent in the sensor, the volume and/or exposed area of the reagent in the sensor, and/or the volume of the cavity within the sensor (which ultimately varies the volume of the sample obtained for measurement). If the processor is configured to one sensor from one lot, and later a sensor from another lot is used within the device, then errors may result from the discrepancies in the specific properties of the sensor used compared to the sensor that the device was calibrated/configured for. Therefore, as with any device, the processor 101 of the present invention must be calibrated to the specific properties of the sensors 201 used by the device 100.

As used herein, the same lot includes: (1) sensors that go through the same manufacturing process at the same time and in the same batch; (2) sensors that go through the same manufacturing process at substantially the same time but in different batches; and (3) sensors that go through the same manufacturing process at different times and in different batches.

In one embodiment, the processor 101 is pre-loaded with the specific properties of the sensors 201 contained therewith. Stated another way, the processor 101 of the device 100 comprises pre-stored calibration data that is unique to the specific sensors contained therein. Therefore, not only does the user not have to enter in any sort of specific calibration code (as required by many prior art devices), but there is also a reduced risk that the devices will be miscalibrated since they are pre-calibrated prior to receipt by the user.

Figure 5:
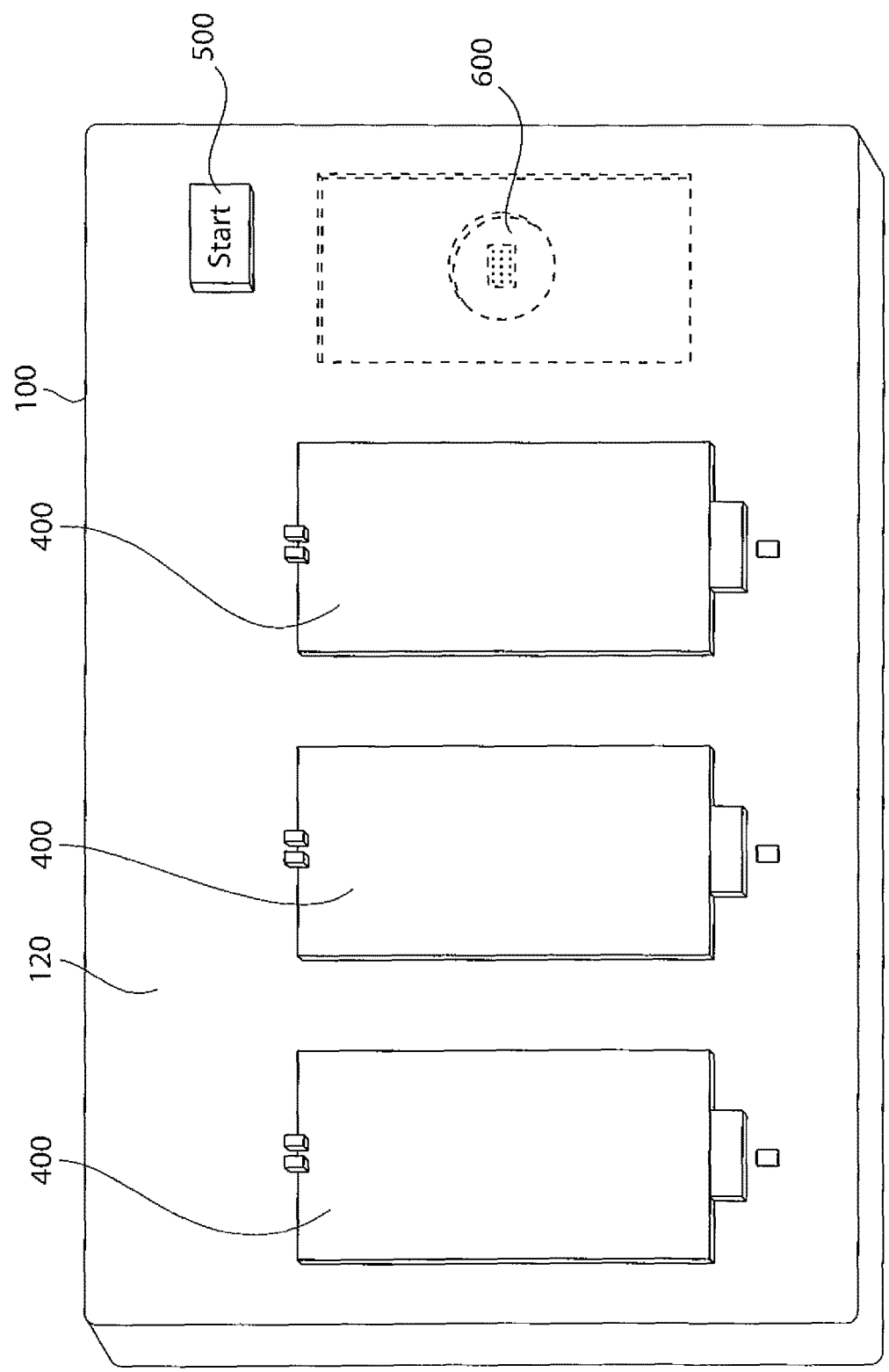
FIG. 5 is a perspective view of the device of FIG. 2 wherein the calibration sensor which is inaccessible to the user is illustrated according to another embodiment of the present invention.

Referring to FIG. 5, the device 100 according to one embodiment of the present invention is illustrated. The device 100 is substantially similar to the devices of FIGS. 4 and 5, except the device 100 of FIG. 5 further comprises a calibration sensor 600. The calibration sensor 600 is substantially similar to and provided from the same lot as the other sensors 201 (not illustrated but provided under their respective covers 400) provided within the device 100. In the exemplified embodiment, the calibration sensor 600 is not viewable or accessible to the user from the outside of the device 100. Since the calibration sensor 600 is from the same lot as the other sensors 201, the calibration sensor 600 has substantially the same specific properties as the other sensors 201 of the device 100, and as a result can be used to pre-calibrate the device 100.

In one embodiment, during the manufacturing of the device 100, a test sample with a known physiological parameter (e.g. a known glucose level) is applied to the sensing element of the calibration sensor 600 and a test signal is generated and transmitted to the processor 101. Since the physiological parameter of the test sample is known, when the processor 101 receives the test signal, the processor 101 can be calibrated for the specific properties of the calibration sensor 600. Further, this test signal and calibration information may then be saved in the memory unit 104 so that accurate measurements are obtained when the other sensors 201 of the device 100 are later used. Also, since the remaining sensors 201 of the device 100 are from the same lot as the calibration sensor 600, the processor is pre-configured for the specific properties of the sensors 201. Further, since the pre-calibration process is done prior to distributing the device 100 to the user, the user is not required to do any calibration steps prior to using the device 100.

In one embodiment, after the calibration sensor 600 is used for calibrating the processor 101 of the device 100, the calibration sensor 600 may be configured so that it is unusable by the user. In one embodiment, the calibration sensor 600 may be configured so that it is unusable by the user by electrically disconnecting the calibration sensor 600 from the processor. In an alternate embodiment, the calibration sensor 600 may simply be inaccessible to the user by, for example, hiding the calibration sensor 600 under the body 120 of the device so not to be viewable by the user.

One method of calibrating the processor 101 of the present invention uses the slope data of a received current level over time when a test sample with a known physiological parameter (e.g. concentration) is applied to the calibration sensor 600. When a test sample with a known physiological parameter (e.g. concentration) is applied to the calibration sensor 600, an electric charge is created under an electrical bias. The current level of the electric charge depends on the physiological parameter (e.g. concentration). Since there is a substantially linear correlation between the current after a certain time and the physiological parameter (e.g. concentration), and since the physiological parameter (e.g. concentration) used on the calibration sensor 600 is known, any sort of deviation of the slope due to the specific properties of the sensors from a specific lot can be calculated and accounted for when using the other sensors 201. The invention, however, is not so limited and in alternate embodiments other methods of calibrating the processor 101 may be used.

In one embodiment, the self-contained an integrated design of the device 100 allows for usage of low costs components as each channel in the voltammetric data acquisition system can be individually calibrated at the time of manufacturing. Therefore, deviations in voltage output and current measurement as well as individual variations in each sensor response can be stored in memory 104.

In one alternate embodiment, the device 100 may further comprise an indication device 300 that indicated that the device 100 is unfit for use because the device 100 has exceeded its pre-determined shelf life. Such calculations can be accomplished by the clock 107 within the processor 101, and thereby prevent invalid readings.

In one embodiment, the device 100 further comprises a button 500 (shown in FIGS. 3 and 4). The button 500 is configured to allow the user to start and power up the device 100 and/or to turn off the device 100. In an alternate embodiment, the device 100 may comprise a plurality of touch buttons allowing for user feedback at the time the measurement of a sensor 201 is taken. For example, the user can be asked to answer a question, the result of the question stored together with the measurement result of the sensor 201 in the memory unit 104. In other alternate embodiments, the device 100 may further comprise a display screen to user interaction and/or feedback.

In other alternate embodiments, the device may further comprises other indication devices 300 (shown in FIG. 3) that indicate other forms of information to the user (e.g. Temperature, Health Status, and/or Wireless Communication). In the exemplified embodiment, the indication devices 300 are LEDs that illuminated to convey information to the user. The invention, however, is not so limited and in alternate embodiments the indication devices 300 may be any other device that can be used to signal information to the user. For example, the indication device 300 may be associated with a temperature reading, whereby the indication device 300 lights up when the temperature reading is too high and/or too low.

Further, in one embodiment, the indication device 300 may be associated with a health status reading, whereby the indication device 300 lights up in one of a plurality of colors to indicate to the user whether the actual physiological level calculated by the processor 101 indicates a physiological level within a healthy physiological range, an unhealthy physiological range, and/or an inconclusive physiological range, depending on the physiological parameter tested. In one alternate embodiment, the indicator may be an LED that flashes or illuminates a different color based on the actual physiological level calculated. Additionally, in an alternate embodiment, the indication device 300 may be associated with a wireless communication reading, whereby the indication device 300 lights up to indicate a successful or failed wireless data transfer.

Figure 6:
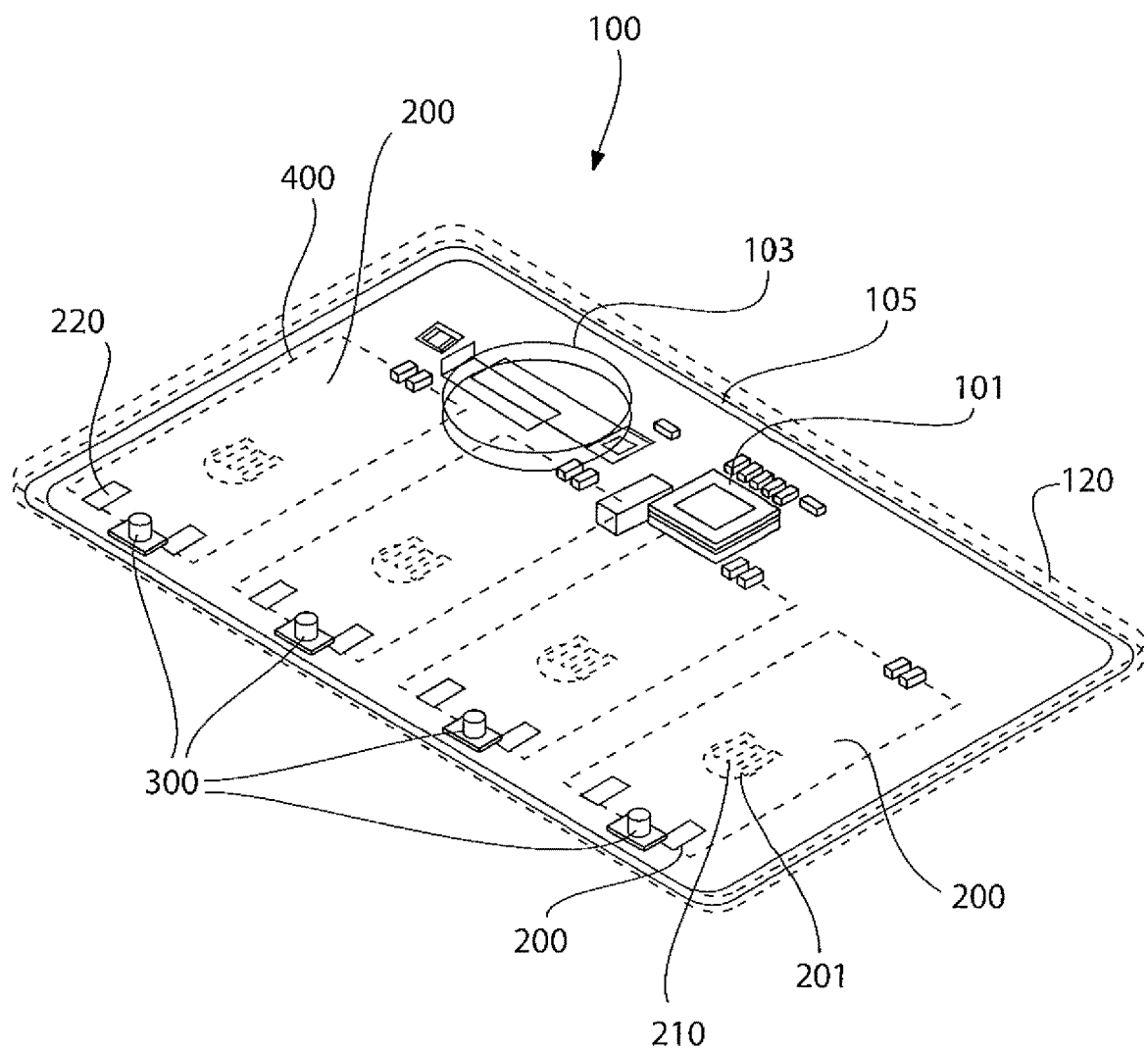
FIG. 6 is a perspective view of another embodiment of the device of the present invention.

Referring to FIG. 6, a device 100 according to another embodiment of the present invention is illustrated. The device 100 of FIG. 6 is substantially similar to the device 100 of FIGS. 2-5.

Figure 7:
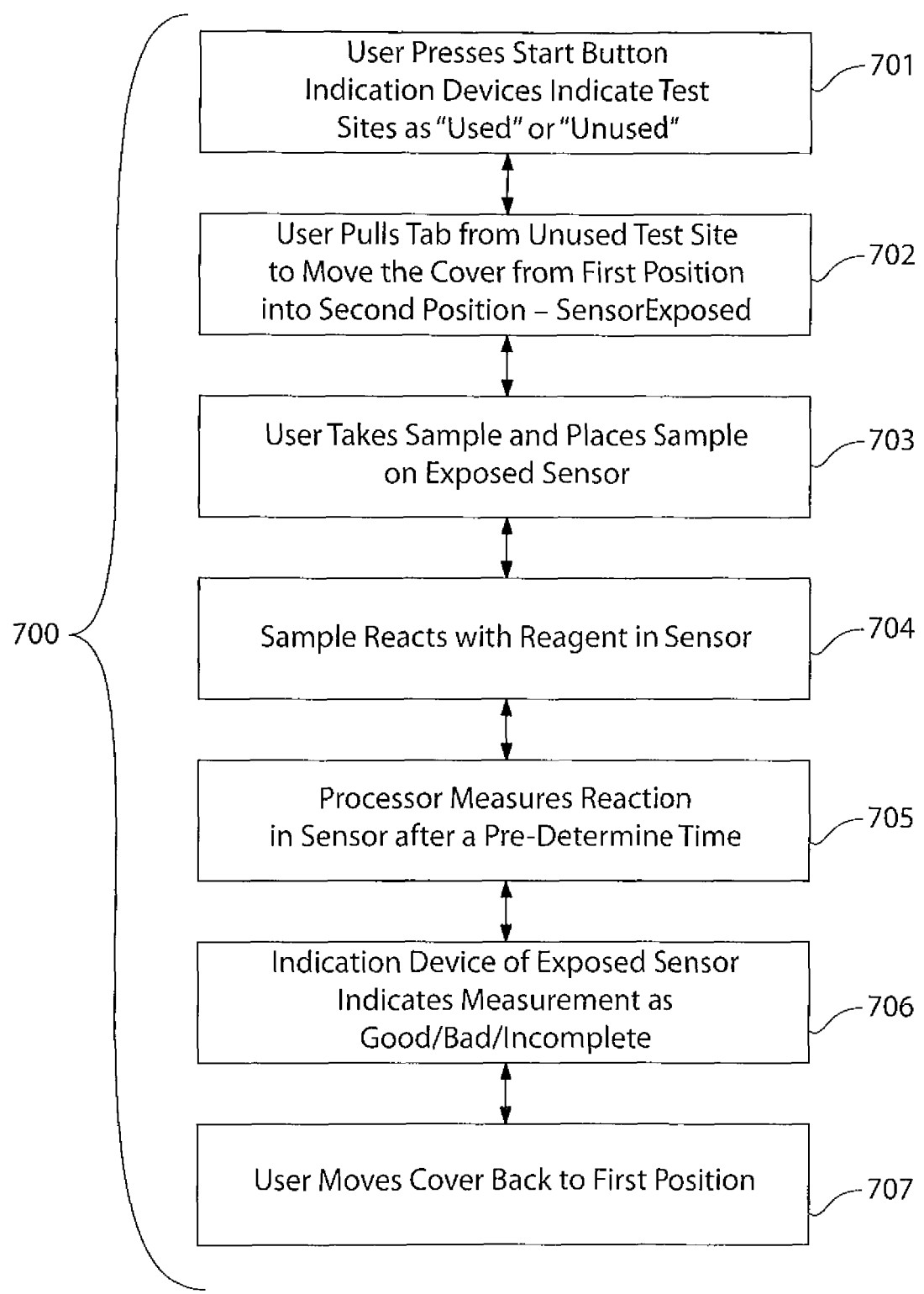
FIG. 7 is a method of using the device of FIG. 2 according to one embodiment of the present invention.

Referring to FIG. 7, a method 700 of using a device 100 according to an embodiment of the present invention is illustrated. At step 701, when the user is ready to take a reading of a physiological parameter (e.g. glucose, cholesterol, etc.), the user first turns on the device 100 and checks which test sites 200 have yet to be used by looking at the indication device 300 associated with each test site 200 (where applicable). Next, at step 702, the user pulls the tab 401 of a cover 400 of an unused test site 200, and peels off the cover 400 (into the second position), thereby exposing the sensor 201. The sensor 201 is qualified to be exposed to the ambient atmosphere for a specific amount of time without affecting the measurement/reading accuracy of the sensor 201.

At step 703, within a reasonable amount of time, the user then places a sample (e.g. a blood sample) on the sensor 201. In one embodiment, the user obtains the blood sample by using a lancet on the tip of one of their fingers, thereby releasing a small amount of their blood. Preferably, the blood sample is placed within the cavity 205 of the sensor 201 and on the reagent 210. At step 704, once the sample is located on the sensor 201, the sample reacts with the reagent 210 in the sensor 201.

As noted above, the removal of the cover from the test site 200 initiates the processor 101 and sensor 201 of the test site 200. Once the sample is located within the cavity 205 of the sensor 201, and after a pre-determined period of time (e.g. 5 seconds), a chemical redox reaction occurs and causes a current flow that is measured by the signal conditional means of the processor 101. By appropriate calculations performed by the data processing means of the processor 101, the current flow and the current decay is converted to a reading, which is then stored in the memory 104 of the device 100. Further, in one embodiment, the reading calculated by the processor 101 is an actual physiological level (e.g. glucose level, cholesterol level, etc.) based on the received signal. The actual physiological level is then stored within the memory device 104.

The sensor 201 design causes the biochemically active material (reagent 210) to be depleted after one measurement of one sample, which means that each sensor 201 can be used only once. Therefore, when the sample is taken and the measurement is complete, the sensor 201 is no longer usable. Further, it should be noted that the sensor redox reaction is a temperature dependent thermodynamic process and the signal conditioning must take a temperature reading from the temperature sensor 105 into account.

At step 706, the indication device 300 of the test strip 200 being used remains on, while the indication devices 300 of the other test strips 200 turn off. As noted above, in some embodiments, the indication device 300 of the sensor 201 being used may be configured to indicate whether the processor 101 is measuring the sample, whether the measurement is successful/unsuccessful.

Finally, at step 707, after the sensor 201 is used and a measurement taken, the cover 400 may be closed (returned to the first position) to prevent the sample from exiting the test site 200. Thereafter, the device 100 may be powered down and put away for another use. Since the device 100, of the present invention may comprise more than one test site 200 (and thus more than one sensor 201), the device may be kept for use at a later time. After all the test sites 200 of the device 100 have been used, the device 100 may be returned to a centralized data processing and diagnostics site where the device 100 is scanned and the information retrieved. At the centralized data processing and diagnostics site, the envelope with the device 100 may be scanned with an RFID scanner and the information retrieved therefrom. In such an embodiment, each device 100 will have a device identification number that is used to link the device to a specific patient. The results of the measurements may then be transmitted in encrypted form to a host system for further analysis and diagnosis. In an alternate embodiment, the information located within the memory of the device 100 may be transmitted (either wirelessly or not) to a remote device, where the information may be viewable by the user and/or a physician/doctor. Thereafter, the device may be thrown away.

It should be noted, that in one embodiment of the present invention, the device 100 is only good for "one use." Stated another way, the test sites 200 (and sensors 201) the device 100 can only be used once, and after they are used, the device 100 may be discarded.

In one embodiment, the device 100 is provided in a package with lancets, sterile wipes for the user's finger and/or card, and a sealable plastic bad to place the device 100 in for disposal.

As noted above, in one embodiment, upon the user peeling the cover 400 off the test site 200 and exposing the sensor 201, an indicator 300 fixed to the body 120 and operably coupled to the processor 101 provides an indication to the user of: (1) whether the glucose sensor has received a sufficient amount of the blood sample; (2) whether the glucose sensor registered an accurate measurement; and/or (3) whether the glucose sensor registered an inaccurate measurement. Further, in an alternate embodiment, prior to the cover 400 being lifted and uncovering the test site 201, but after the device 100 is turned on, the indicator 300 may further provide an indication to the user of whether the sensor 201 has been previously used.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

What is claimed is:

1. A portable apparatus for measuring a glucose level of a user comprising:
    a thin, generally flat substrate housing member having opposing substantially planar surfaces;
    a processor disposed within said housing member;
    at least one test site comprising a glucose sensor for generating a signal indicative of a measured glucose level upon application of a blood sample to the glucose sensor, wherein the glucose sensor comprises a cavity fixed to said housing member and operably coupled to the processor and wherein the reagent is substantially within said cavity;
    a calibration glucose sensor fixed to the housing member so as to be unusable by the user and wherein calibration data unique to the at least one glucose sensor is generated by the calibration glucose sensor; and
    at least one cover alterable between a first position in which the glucose sensor is covered and a second position in which the glucose sensor is exposed for use.

2. The apparatus of claim 1 wherein the processor receives the signal indicative of the measured glucose level from the glucose sensor and calculates an actual glucose level based on the received signal, the apparatus further comprising a memory device operably coupled to the processor, the processor storing the actual glucose level within the memory device.

3. The apparatus of claim 2 further comprising an indicator configured to indicate whether the actual glucose level calculated by the processor indicates a glucose level within a healthy glucose level, an unhealthy glucose level, or an inconclusive glucose level.

4. The apparatus of claim 1 further comprising an indicator fixed to the housing member and operably coupled to the processor to provide an indication to the user of: (1) whether the at least one glucose sensor has been previously used; (2) whether the at least one glucose sensor has received a sufficient amount of the blood sample; (3) whether the at least one glucose sensor registered an accurate measurement; and/or (4) whether the at least one glucose sensor registered an inaccurate measurement.

5. The apparatus of claim 1 further comprising a memory device within the housing member and operably coupled to the processor, the memory device comprising pre-stored calibration data unique to the at least one glucose sensor.

6. The apparatus of claim 5 wherein the calibration glucose sensor being is from the same lot as the at least one glucose sensor, and further wherein the pre-stored calibration data unique to the glucose sensor is generated by the calibration glucose sensor and stored in the memory device.

7. The apparatus of claim 6 wherein the calibration glucose sensor is embedded within the housing member.

8. The apparatus of claim 6 wherein the calibration data unique to the glucose sensor is generated by the calibration glucose sensor by:
    applying a test solution having a known glucose level to the calibration glucose sensor, the calibration glucose sensor generating a test signal indicative of a measured glucose level of the test solution; and
    the microprocessor receiving the test signal and generating the pre-stored calibration data for storage on the memory device.

9. The apparatus of claim 1 further comprising a temperature sensor operably configured to measure ambient temperature and/or temperature of the at least one glucose sensor and generate a temperature signal indicative of the measured ambient temperature and/or temperature of the glucose sensor, the temperature sensor operably coupled to the microprocessor.

10. The apparatus of claim 9 further comprising an indicator configured to indicate whether the ambient temperature and/or temperature of the at least one glucose sensor is above a threshold value.

11. The apparatus of claim 1 further comprising a protective seal sealing the at least one glucose sensor, the protective seal disposed between the at least one glucose sensor and the cover.

12. The apparatus of claim 1 further comprising a wireless communication device operably coupled to the processor and configured to transmit a transmission signal generated by the processor to an external device.

13. The apparatus of claim 12, wherein the wireless communication device is a passive, semi-passive or active RFID or a wireless local area networking enabled device.

14. The apparatus of claim 12 wherein the processor receives the signal indicative of the measured glucose level from the at least one glucose sensor and calculates an actual glucose level based on the received signal, the apparatus further comprising a memory device operably coupled to the processor, the processor storing the actual glucose level within the memory device, and wherein the transmission signal is indicative of the actual glucose level.

15. The apparatus of claim 1 wherein the reagent is glucose oxidase, glucose dehydrogenase/pyrroloquinoline-quinone, dehydrogenase/nicotinamide-adenine dinucleotide, or dehydrogenase/flavin-adenine dinucleotide.

16. A portable apparatus for measuring a physiological condition comprising:
    a planar design comprising a thin, generally flat housing member having opposing substantially planar surfaces;
    a processor integrally formed within the housing member;
    at least one physiological parameter sensor for generating a signal indicative of a measured physiological parameter upon application of a blood sample to the sensor, wherein said physiological parameter sensor comprises a cavity fixed to said housing member and a reagent and further wherein said physiological parameter sensor is operably coupled to the processor and wherein the reagent is substantially within said cavity
    a calibration physiological parameter sensor fixed to the housing member so as to be unusable by the user and wherein calibration data unique to the at least one sensor is generated by the calibration physiological parameter sensor and wherein the physiological parameter sensor is configured in the same level and on the same substrate that holds the calibration physiological parameter sensor and
    at least one cover alterable between a first position in which the sensor is covered and a second position in which the sensor is exposed for use.

17. The apparatus of claim 16 wherein the physiological parameter is a glucose level, cholesterol level, blood urea nitrogen (BUN) level and/or creatinine level.

18. The apparatus of claim 16 wherein the processor receives the signal indicative of the measured physiological parameter from the sensor and calculates an actual physiological level based on the received signal, the apparatus further comprising a memory device operably coupled to the processor, the processor storing the actual physiological level within the memory device.

19. The apparatus of claim 16 further comprising a memory device within the housing member and operably coupled to the processor, the memory device comprising pre-stored calibration data unique to the sensor.

20. The apparatus of claim 19 wherein the calibration physiological parameter sensor is embedded within the housing member.

21. The apparatus of claim 19 wherein the calibration data unique to the physiological parameter sensor is generated by the calibration physiological parameter sensor by:
    applying a test solution having a known physiological level to the calibration physiological parameter sensor, the calibration physiological parameter sensor generating a test signal indicative of a measured physiological level of the test solution; and
    the processor receiving the test signal and generating the pre-stored physiological parameter calibration data for storage on the memory device.

22. The apparatus of claim 16 further comprising a temperature sensor operably configured to measure ambient temperature or temperature of the at least one sensor and generate a temperature signal indicative of the measured ambient temperature or temperature of the at least one sensor, the temperature sensor operably coupled to the processor.

23. The apparatus of claim 22 further comprising an indicator configured to indicate whether the ambient temperature or temperature of the at least one sensor is above a threshold value.

24. The apparatus of claim 16 further comprising a protective seal sealing the at least one sensor, the protective seal disposed between the at least one sensor and the cover.

25. The apparatus of claim 16 further comprising a wireless communication device operably coupled to the processor and configured to transmit a transmission signal generated by the processor to an external device.

26. The apparatus of claim 25, wherein the wireless communication device is a passive, semi-passive or active RFID or a wireless local area networking enabled device.

27. The apparatus of claim 25 wherein the processor receives the signal indicative of the measured physiological level from the at least one sensor and calculates an actual physiological level based on the received signal, the apparatus further comprising a memory device operably coupled to the processor, the processor storing the actual physiological level within the memory device, and wherein the transmission signal is indicative of actual physiological level.

* * * * *